United States Patent [19]
Romaine et al.

[11] Patent Number: 4,803,800
[45] Date of Patent: Feb. 14, 1989

[54] SYNTHETIC SUBSTRATE FOR FILAMENTOUS FUNGI

[75] Inventors: C. Peter Romaine, Boalsburg, Pa.; Charles E. Nelsen, Davis; Roxanne Davis, Sacramento, both of Calif.

[73] Assignee: Plant Genetics, Inc., Davis, Calif.

[21] Appl. No.: 31,512

[22] Filed: Mar. 27, 1987

[51] Int. Cl.4 .......................... A01G 1/04; C05G 1/00
[52] U.S. Cl. ............................................. 47/1.1; 71/5; 71/64.09
[58] Field of Search ............... 47/1.1, 58; 71/5, 64.01, 71/64.03, 64.09, 64.11, 64.13

[56] References Cited

U.S. PATENT DOCUMENTS

| | | | |
|---|---|---|---|
| 2,091,993 | 9/1937 | Jones | 47/58 X |
| 3,639,259 | 2/1972 | Scarpelli | 71/64.09 |
| 4,337,594 | 7/1982 | Hanacek et al. | 47/1.1 |
| 4,345,931 | 8/1982 | Meyer | 71/28 |
| 4,370,159 | 1/1983 | Holtz | 71/5 |
| 4,551,165 | 11/1985 | Warner | 47/1.1 X |
| 4,581,846 | 4/1986 | Stensaas | 47/1.1 X |
| 4,589,225 | 5/1986 | Stensaas | 47/58 |
| 4,722,159 | 2/1988 | Watanabe et al. | 47/1.1 |

FOREIGN PATENT DOCUMENTS 1308614  2/1973  United Kingdom ................. 71/64.9

Primary Examiner—Robert E. Bagwill
Attorney, Agent, or Firm—Limbach, Limbach & Sutton

[57] ABSTRACT

A synthetic substrate which supports the growth and development of filamentous fungi is disclosed. The substrate is comprised of a nutrient in a hydrated hydrogel matrix forming a capsule. In a preferred embodiment, the capsule has an irregular external surface to allow filamentous fungi to adhere thereto even when shaken. Also disclosed is a synthetic CACing agent which includes the synthetic substrate of the present invention, a method of manufacturing the synthetic substrate of the present invention and a method of cultivating mushroom spawn and cultivating mushrooms utilizing the synthetic substrate.

113 Claims, No Drawings

SYNTHETIC SUBSTRATE FOR FILAMENTOUS FUNGI

DESCRIPTION

TECHNICAL FIELD

The present invention relates generally to the field of mycology. More specifically, the present invention relates to a synthetic substrate for supporting growth of filamentous fungi, a process for making the same and a process for utilizing the same in the cultivation of mushrooms.

BACKGROUND OF THE INVENTION

Fungi are microscopic, spore-bearing organisms which lack chlorophyll and therefore derive nourishment from dead or living organic matter. Alexopoulos, C. J., et al., *Introductory Mycology* (1979), Chapter 1. Because they share characteristics of both plants and animals, they are classified separately in the Kingdom Myceteae. Within this Kingdom, there are the "filamentous fungi", so named because their vegetative bodies consists of small filaments referred to as "hyphae". Typically, the hyphae grow in a branching fashion, spreading over or within the substrate used as the source of nourishment, thereby forming a network of hyphae called "mycelium". In the life cycle of most filamentous fungi, the mycelium gives rise to either asexual or sexual reproductive bodies bearing spores. The spore is functionally comparable to the seed of higher plants, being important in the dispersal and survival of the fungus in nature. Under suitable environmental conditions, the spore germinates to form another generation of hyphae and so completing the life cycle of the fungus.

Filamentous fungi play an important role in numerous industrial processes. Such fungi are utilized in fermentation systems ("bioreactors") for the commercial production of organic acids, drugs (e.g., ergometrine and cortisone), and antibiotics (e.g., penicillin and griseofulvin). Alexopoulos, C. J., et al., *Introductory Mycology* (1979), p. 5. Fungi are also valued for their unique biological activities which enhance the growth and productivity of other, usually higher, plants. For example, some fungi (e.g., mycorrhizal fungi) inhabit the roots of higher plants, and render the plant more tolerant of heavy metals, pathogens, drought, temperature, pH and transplant shock. Schenck, N. C., *Methods and Principles of Mychorrhizal Research* (1982), p. ix. Still other filamentous fungi can suppress the activities of plant pathogens and, consequently, are being exploited in the control of plant diseases (biological control fungi). Cook, R. J., et al., *The Nature and Practice of Biological Control of Plant Pathogens* (1983), p. 539.

Perhaps filamentous fungi are best known for their edible, fleshy, spore-bearing, reproductive structures called "mushrooms". Mushrooms have been grown commercially for many years. Throughout these years, commercial production of cultivated mushrooms has increased dramatically. In 1939, worldwide production of *Agaricus bisporus* (also referred to as *Agaricus brunnescens*), the most popular of the edible cultivated mushrooms, was 46,000 tons. Flegg, P. B. and Wood, D. A., *The Biology and Technology of the Cultivated Mushroom*. Chapter 1, p. 7 (1985). By 1982, that figure was in excess of 850,000 tons. Id.

The common edible mushroom (e.g., *A. bisporus*) has both vegetative and reproductive ("fruiting") forms. The form most familiar to consumers is the fruiting form (i.e., mushroom) which has a stalk and an umbrella shaped cap. The life cycle of this mushroom fungus begins with the germination of a spore, which produces hyphae. A collection of hyphae compact together and form the mycelium. The mycelium then grow and invade the environment as networks. Small masses at the periphery of the network of mycelium enlarge and differentiate to form immature mushrooms called "buttons". The buttons rapidly enlarge and burst through the soil and become mature mushrooms. Mushrooms are produced from mycelium in cycles referred to as "breaks" or "flushes". A single population of mycelium may produce multiple breaks. The mushrooms then produce spores which germinate and produce further mycelium.

Methods of commercial mushroom cultivation are well known and generally involve inoculating compost rich in (See Carroll, Jr. et al., U.S. Pat. No. 3,942,962.) As used herein, the term "spawn" refers to a nutrient substrate colonized by mycelium. In the process referred to as "spawning," the spawn is mixed with compost to promote growth of the mycelium throughout the compost. The compost is usually comprised of straw bedded horse manure or other combination of fibrous plant material. Several weeks after spawn dissemination, when the compost has been sufficiently colonized by the fungus, the compost is covered with a thin layer of "topsoil" (e.g., peat, soil). This process is called "casing" and the layer of topsoil is sometimes referred to as "casing material". Within weeks of casing, mushrooms develop and are harvested in breaks. Precisely how the process of casing induces mushroom formation is unclear. However, there is supportive evidence for the role of bacteria, in particular Pseudomonas spp., in this phenomenon. Eger, G., *Mushroom Science VIII* (1972), pp. 719–725. In a variation of the standard casing procedure called "CACing" ("compost-at-casing"), compost colonized by mushroom fungus is mixed with the casing material and then applied to the colonized compost. This procedure is known to be particularly effective on *Agaricus bisporus*. The result is an earlier and more uniform development of mushrooms. MacCanna, C., et al., *Mushroom Science VIII* (1972), pp. 727–731.

Throughout the history of mushroom cultivation, a variety of substrates have been employed in the production of spawn. In one conventional method known as the "compost method", the spawn comprises compost from which fruiting bodies were previously grown and which contain the mycelium of another generation of mushrooms ("parental compost"). This parental compost-type spawn is used to inoculate a further quantity of uninoculated compost ("crop compost"). The parental compost may contain many other organisms which may flourish along with, or compete with, mycelium or mushrooms. As can be appreciated, spawn that is comprised of parental compost cannot be sterilized since sterilization will also destroy the valuable mycelium contained therein. Thus, methods have been devised where crop compost is treated with certain agents so as to promote growth of mycelium and mushrooms but inhibit growth of other interfering organisms which may be present in the parental compost. Such treatments of crop compost, however, do not solve the problem of pathogens which may be present in the parental compost and which may be transmitted from one generation of spawn to the next. In order to contain this problem, methods have been devised whereby the entire process is highly controlled and maintained under sterile conditions.

Currently, the grain substrate method is the most widely used for commercial mushroom cultivation. Although a few spawn producers use barley as grain substrate, rye grain and millet grain are predominantly used by most of the industry. In this method, the substrate provides a surface area onto which mycelium may adhere and grow as well as a nutrient source for the vegetative bodies. A quantity of grain is first sterilized and inoculated with cultivated mycelium. Only a small amount of grain supply need be inoculated because the mycelium grows and inoculates the surrounding grain substrate. Uniform substrate inoculation is promoted by shaking, or otherwise mixing, the inoculated substrate throughout the substrate supply. Once the mycelium has sufficiently colonized the substrate supply, the resulting spawn is disseminated in compost for the production of mushrooms. This method is advantageous over the compost method because sterility is more easily maintained.

The prior art methods discussed hereinabove suffer from the disadvantage that they allow little control over the nutrient composition, water content, osmolarity and pH of the spawn substrate. These factors, considered singularly or collectively, would impact directly on the growth, development and fruiting of filamentous fungi.

It is, therefore, an object of the present invention to provide a method for cultivating mushroom spawn under sterile conditions.

It is another object of the present invention to provide a method for cultivating mushroom spawn with a uniform and reproducible nutrient source.

It is yet another object of the present invention to provide a method for cultivating mushroom spawn where the water content, osmolarity and pH of the substrate may be regulated.

It is another object of the present invention to provide a method of cultivating mushroom spawn and introducing the same into compost for the production of mushrooms.

It is another object of the present invention to provide a method for cultivating a synthetic CACing agent and introducing the same into a casing layer for the production of mushrooms.

It is another object of the present invention to provide a method for cultivating mushroom spawn and mushrooms where the substrate for filamentous fungi includes substances which enhance the growth, development and fruiting of fungi.

It is a further object of the present invention to provide a synthetic substrate for filamentous fungi.

It is yet a further object of the present invention to provide a synthetic substrate onto which filamentous fungi may adhere.

It is still another object of the present invention to provide a sterile synthetic substrate for filamentous fungi.

It is yet another object of the present invention to provide a synthetic substrate for filamentous fungi that is uniform in size and composition.

It is an additional object of the present invention to provide a synthetic substrate for filamentous fungi including a nutrient source.

It is yet another object of the present invention to provide a synthetic substrate for filamentous fungi in which the water content, osmolarity and pH may be regulated.

It is still another object of the present invention to provide a synthetic substrate for filamentous fungi including growth controlling agents which effect the growth, development and fruiting of fungi.

It is another object of the present invention to provide a synthetic substrate for filamentous fungi including biological agents such as bacteria, nematodes, fungi, viruses and protozoa for the cultivation of filamentous fungi or mushrooms.

It is another object to provide a method of making the synthetic substrate of the present invention.

SUMMARY OF THE INVENTION

The present invention provides methods and compositions for the cultivation of filamentous fungi, mushroom spawn and mushrooms with a synthetic substrate. The substrate of the present invention is comprised of a nutrient medium capable of sustaining growth of filamentous fungi in a hydrated hydrogel matrix capsule. The capsule should be capable of supporting growth of filamentous fungi on substantially its entire surface.

The present invention also provides a synthetic CACing agent comprising the synthetic substrate of the present invention dispersed in a medium.

The present invention also provides a method for manufacturing the synthetic substrate of the present invention comprising the steps of providing a nutrient medium capable of sustaining mycelial growth in a hydrated hydrogel matrix capsule.

Also provided is a method of cultivating filamentous fungi utilizing the synthetic substrate of the present invention. The process includes the step of inoculating the external surface of the above-described capsule with filamentous fungi.

A method of cultivating mushrooms is also provided. The method includes the step of dispersing the above described inoculated capsule into a medium which permits fungi to produce mushrooms.

These and other aspects of the present invention can be better appreciated from the following detailed description of the invention.

BEST MODE FOR CARRYING OUT THE INVENTION

The present invention provides a novel synthetic substrate for filamentous fungi (e.g., mycelium) which comprises a surface onto which filamentous fungi may grow and a nutrient reserve for the fungi. The nutrient reserve may be comprised of any medium containing substances from which filamentous fungi may derive appropriate nourishment for growth and development. In accordance with the present invention, such a growth surface and nutrient reserve are provided by a synthetic substrate comprised of nutrient medium included in a substance forming a capsule having an external surface onto which filamentous fungi may grow. In accordance with the present invention, the nutrient reserve may be included in any of the various media, hydrated hydrogels (i.e., hydrophilic gel agent in the presence of water) or polymers, which provide an appropriate matrix, hereinafter termed "gel". Thus, the nutrient medium may be said to be included in a "gel matrix" (or a "hydrated hydrogel matrix" where the gel agent is a hydrated hydrogel).

In general, the gel matrix used in the present invention should provide a surface onto which filamentous fungi may grow on substantially the entire capsule surface and sufficient structural integrity to maintain the capsule components so that the resultant capsule may reasonably resist damage due to external abrasion and internal pressure from the contents thereof. Although mere physical distortion of the capsule is tolerable, the capsule should substantially resist physical damage. Further, the gel matrix must allow filamentous fungi on the external surface of the capsule to have access to the nutrient reserve and other materials included therein. This objective may be accomplished by providing a gel matrix which will allow the fungus to physically or physiologically access the interior of the capsule to invade the nutrient reserve contained therein, such as a fissure or a plurality of fissures in the capsule surface, by providing nutrients which diffuse through a gel matrix, or by providing a gel matrix which is digestible by secretions of the fungus (e.g., enzymes). Further, because the shelf life of the inoculated synthetic substrate is dependent upon the availability of water in adequate supply, the gel matrix should additionally be able to withstand substantial water loss when the substrate inoculated with the fungus is stored or transported.

Gels finding use as the gel agent of the substrate of the present invention include hydrated hydrogels or polymers which contain water within the confines of the gel matrix. It may, in some instances, be desirable to use various gels in combination, either as a mixture or in layers. Gels which have been found to be useful for such purposes include sodium alginate, potassium alginate, polygalacturonic acid and a mixture of gelatin and sodium alginate. Other suitable polymers include, but are not limited to, the gels listed in Table A below.

TABLE A

I. Natural Polymers
   A. Ionic bonds (requires complexing agents)
      Alginate with Gelatin
      Sodium Pectate
      Furcellaran
      Pectin
      Hypnean
      Dextran
      Tamarind
      Guar Gum
   B. Hydrophobic Interactions
      Amylose
      Agar
      Agarose
      Agar with Gelatin
      Gelatin
      Starch
      Amylopectin
      Cornhull Gum
      Starch Arabogalactan
      Gum Ghatti
      Gum Karagan
      Ti Gum
      Gum Tragacanth
      Wheat Gum
      Chitin
      Dextrin
II. Chemically Modified Natural Polymers
   A. Ionic Bonds (requires a complexing agent)
      Ethyl Succinylated Cellulose
      Succinylated Zein
      Carboxymethylcellulose
   B. Hydrophobic Interactions
      Methylcellulose
      Hydroxyethyl Cellulose
   C. Covalent Bonds
      Gelatin with Glutaraldehyde
III. Synthetic Polymers TABLE A-continued A. Covalent Bonds
      Polyacrylamide
   B. Hydrophobic Interactions
      Polyethylene Glycol
      Polyvinylpyrrolidone
      Polyoxyethylene
      Hydrophilic Urethane
      Polyvinylacetate
      Vinyl Resins
      Hydron (hydroxyethylmethacrylate)
      2-methyl-5-vinylpyridine-methylacrylate-methacrylic acid
   C. Ionic Bonds
      Sodium poly (styrene sulfonate) with poly (vinyl methyl pyridinium) chloride
      Sodium poly (styrene sulfonate) with poly (vinyl benzyl trimethyl ammonium) chloride
      Strongly acidic polyanion with strongly basic polycation
      Bordon Poly Co. 2113 ® (vinyl acetate homopolymer) (Borden Co.)
      Gelvatol ® (polyvinyl alcohol resin) (Monsanto)

Once the gel has been chosen, there are numerous parameters which influence the character of the gel matrix. A sodium alginate solution, for example, will form a gel when a complexing agent is added. Calcium chloride ($CaCl_2$) is typically used as the complexing agent. However, other calcium salts such as calcium nitrate and calcium hydroxide are useful complexing agents. Copper salts (particularly copper sulfate), chitosan (a deacylated chitin), potassium chloride, ammonium chloride, lanthanum chloride, ferric chloride, cobaltous chloride, sodium tetraborate, superphosphate fertilizer, and many common pesticides such as benefin, alachlor and chlorpropham are also acceptable, as are other compounds generally with multivalent cations.

Any particular gel will have a range of acceptable concentrations in practicing the present invention. The gel concentration should be chosen to optimize ease of handling, gelling time, strength of gel and capsule size. Sodium alginate gel mixture, for example, can be prepared at a concentration of 0.4 to 10% by weight in grams sodium alginate/milliliters water, and preferably from 0.5 to 5%.

To encapsulate the nutrient medium and other materials in the gel matrix, they may be inserted into preformed gel capsules. Alternatively, the capsule components may be dispersed into the gel solution and capsules may be formed by removing the dispersion in drops. In either case, the gel must be complexed. In some cases, depending upon the gel agent used, complexing will require or, at least, be enhanced with a complexing agent. Numerous techniques for mixing gel solution with complexing agent are known in the art. In one technique, the gel mixture is added dropwise to a solution containing the complexing agent. In another technique, droplet formation and complexing agent addition is performed as a one step process utilizing a vibrating nozzle which ejects a gel droplet from one source and coats the droplet with a complexing agent from another source.

The concentration of the complexing agent is also important to the quality of the capsule formed. For example, when $CaCl_2$ is the complexing agent, it should be at a concentration in the range of 1 to 1,000 millimolar, usually 20 to 500 millimolar and preferably 50 to 300 millimolar. As can be appreciated, other complexing agents will have different preferred concentration ranges.

The time for gel formation and the temperature of the gel mixtures are interrelated parameters for selected concentrations of gel and complexing agent. Where the capsule does not contain living biological material, no specific temperature limits apply. However, where living biological matter (e.g., fungi, nematodes or bacteria) are contained within the gel matrix, the temperature should be chosen so as to avoid altering the character of those living capsule components. Suitable temperatures are usually in the range of 1 to 40 degrees centigrade, preferably 10 to 35 degrees centigrade.

Within the range of acceptable temperatures, a particular value can be chosen to give the shortest possible gelling time consistent with complete gel formation. Typically, the gel skin will form immediately, but complete complexation of the gel takes much longer. For a gel solution of sodium alginate at a concentration of 1.0 grams per 100 milliliters water, a $CaCl_2$ concentration of 100 millimolar and a reaction temperature of 25 degrees centigrade, adequate gelling is obtained in 5 to 120 minutes, more often 10 to 90 minutes, and is usually sufficiently complete in 20 to 60 minutes. Alternatively, other concentrations of the $CaCl_2$ complexing agent can be used which will affect gelling time.

The gel characteristics described above are modifiable for each gel agent, but are determined generally by the concentration parameters and chemical properties of the particular gel agent. Suitable capsule mass is in the range of 20 to 150 milligrams, preferably, 20 to 50 milligrams.

Although the fungus is able to grow on the surface of the gel capsule thus comprised, disruption of the inoculated carrier by shaking often causes some of the mycelium to slough off of the substrate surface, which is relatively smooth in texture. Thus, it may be desirable to inoculate the substrate in a procedure where the capsule supply is spread in a thin layer so as to maximize the substrate surface area available for inoculation for a given amount of capsules and thus eliminate the need for shaking. Such a procedure will, of course, require a substantially large quantity of filamentous fungi for the initial inoculation.

Alternatively, it has been discovered that the affinity of fungi for the substrate may be enhanced by texturizing the external surface of the gel capsule so as to create surface irregularities. The mycelium is better able to adhere to such irregular surfaces than to smooth gel surfaces even when shaken. The synthetic substrate of the present invention thus constructed may be easily incorporated into procedures currently being used (i.e., the inoculated carrier supply may be periodically shaken to promote uniform inoculation).

A texturized external gel surface may be obtained by physically altering the gel capsule surface with a texturizing agent which may accomplish this objective by physical abrasion or chemical alteration of the otherwise smooth gel surface. The texturizing step may be carried out subsequent to or during capsule formation. In general, the texturizing agent should have the ability to impart the desired irregularity to the otherwise smooth gel surface and yet not unduly interfere with the formation or integrity of the resultant gel capsules. Where the texturizing step occurs subsequent to capsule formation, either by physical abrasion or chemical alteration, it is important that the gel capsule not be unduly deformed by texturizing. Where the texturizing step occurs during capsule formation, the texturizing agent will most likely be added as a component of the mixture of gel agent, nutrients, etc., to be added dropwise into a solution of complexing agent. In such a case, it is desirable to select a texturizing agent which will not unduly interfere with the flow and formation of the capsule mixture drops.

Substances which have been found to be effective texturizing agents include, but are not limited to, particulate or granular materials which are substantially insoluble in the capsule gel matrix, although they preferably have moisture absorbent properties. Where they are solid in state, they generally should have a dimension in the range of 100 to 6,000 microns, and preferably in the range of 500 to 2,000 microns. They may be organic or inorganic. Substances which have been successfully used as texturizing agents thus far include minerals, puffed minerals, polymers and starches. More specifically, the list of suitable texturizing agents include: hygramer (an inert polymer capable of absorbing approximately five times its weight in water, typically 500 to 2,150±50–100 microns, obtained from Polysystems, Ltd., Bearsden, Glasgow, Scotland G663NY); vermiculite (light weight, heat-resistant granules of puffed minerals, usually micas, or a combination of such minerals, typically 500 to 800 microns, obtained from W. R. Grace and Company, Cambridge, Mass.); TerraSorb® (a starch, synthetic polymer, or combination of the same, capable of absorbing hundreds of times its weight in water, typically 2,000 to 3,000 microns, obtained from Industrial Services International, Inc., Bradenton, Fla.); ground perlite (an expanded volcanic pumice, in the range of 100 to 6,000 microns, e.g. PA-lite 20 perlite ,obtained from Pennsylvania Perlite Corp., York, Pa. 17402); cellulose fiber (in the range of 100 to 6,000 microns, e.g., alpha cellulose obtained from Sigma Chemical Co., St. Louis, Mo. 63178); silica gel (molecular sieve in the range of 8–12 mesh, obtained from J. T. Baker Chemical Co., Phillipsburg, N.J. 08865); grits, particularly soy grits (usually 20 to 40 U.S. Standard mesh, e.g., Nutrisoy defatted soy grits, obtained from Archer Daniels Midland Co., Decatur, Ill. 62528); ground rice hulls (500 to 6,000 microns); ground rice (1,000 to 4,000 microns); ground walnut shells (10 to 20 U. S. Standard mesh); sawdust (600 to 850 microns); sand (20 grade); and ground egg shells (500 to 6,000 microns).

The mechanism of how these texturizing agents achieve their objective of creating irregularities on the external surface of capsules is not precisely known. However, without precluding other theories of operation and without limiting the scope of the present invention, Applicants hypothesize several possible mechanisms which are based upon the physical characteristics of the substances which have heretofore been successfully used as texturizing agents.

All of the substances so far used are solid in state and are substantially insoluble in the fluid environment of the gel mixture or gel matrix under the conditions used for capsule formation and their subsequent use or storage. Within this category of substances are those which have the ability to absorb relatively large amounts of moisture (e.g , hygramer, vermiculite, TerraSorb ®).

We hypothesize that these texturizing agents function by protruding outward from the center of the capsule and under the gel surface to create hills, valleys, fissures and rifts on the external capsule surface. The moisture absorbent texturizing agents may additionally cause surface irregularities by absorbing and/or localizing the fluid component of the gel capsule at various portions of the capsule in which they are disposed. The irregularities may result from expansion of the particles of texturizing agent at or near the surface of the capsule such they protrude outward from the interior of the capsule. Alternatively, or in combination therewith, the particles of texturizing agent may draw capsule moisture toward them and thus cause the capsule surface to pucker inward at various points creating hills, valleys, fissures and rifts.

The texturizing agent should be present in the gel mixture at a concentration sufficient to produce the desired irregular capsule surface. However, because addition of these texturizing agents will increase the viscosity of the gel mixture, their concentrations must be within a range which will not unduly interfere with the formation of the gel capsules. Optimum concentrations, of course, will vary with the particular texturizing agent chosen. Generally, where capsules are formed by gravity the texturizing agent should be present in the gel mixture at a concentration of at least 1% weight texturizing agent/volume gel mixture, and preferably 2 to 6%. No absolute upper limit exists for the concentration of texturizing agent because any difficulties encountered in capsule formation due to increased viscosity of the gel mixture may be remedied by forming the capsules under a pressure sufficient to allow adequate capsule formation.

The nutrient reserve contained within the gel matrix must, of course, provide nourishment for the growth and development of the fungus. Suitable nutrients include, but are not limited to, monosaccharides, oligosaccharides, polysaccharides, sugar acids, alcohols, sugar alcohols, sodium acetate, fatty acids, oils, fats, waxes, amino acids, proteins, nucleosides, nucleotides, sterols, vitamins, cofactors, inorganic compounds, brewer's grain, soybean and soybean derivatives, safflower oil, potato dextrose, alfalfa meal, sugar beet pulp, yeast extract, malt extract, starch, cellulose, hemicellulose, lignocellulose, lignin, compost and others. Nutrient media may also be comprised of broths prepared from the substances listed above. Where the nutrient is also particulate in nature, it may also serve as a texturizing agent (e.g., soy grits).

The nutrient medium should be of a concentration such that sufficient nutrient is provided to sustain growth of the fungus and yet not unduly interfere with the formation of gel capsules by affecting the viscosity and complexing ability of the gel mixture. As can be appreciated, the optimum nutrient concentration will vary with the particular nutrient to be utilized. Generally, the concentration should be at least 1% weight nutrient/volume gel mixture, and preferably 2 to 6%, where capsules are formed by gravity. Like the texturizing agent, no absolute upper limit exists for the concentration of nutrient because any difficulties encountered in capsule formation due to increased viscosity of the gel mixture may be remedied by forming the capsules under a pressure sufficient to allow adequate capsule formation.

The gel capsule of the present invention may contain components other than nutrients for the filamentous or mycelial phase such as a water supply, which may be varied, and nutrients for the formation of the reproductive structures (e.g., a slow release denatured protein). Further, uniformity in size and composition of such capsules may be insured. Other possible capsule inclusions are those which will enhance the growth, development and fruiting of fungi. These include growth controlling agents, such as hormones, as well as biological agents.

Certain nematodes have been known to be effective biological control agents for protection of fungus against pests. Richardson, P. N., "The Use of Rhabditid Nematodes for the Biological Control of Mushroom Flies", *Fundamental and Applied Aspects of Invertebrate Pathology* (1986, Foundation of the Fourth International Colloquium on Invertebrate Pathology, Eds. Sampson, R. A., et al.) More specifically, the nematodes *Heterorhabditis heliothidis*, *Neoaplectana carpocapsae* and *Neoaplectana bibionis* have proven to be effective biological control agents for the "mushroom fly". Id. It has been suggested that certain bacteria may enhance fungal growth and development. There is evidence that bacteria belonging to the genus Pseudomonas have such an effect on *Agaricus bisporus*. Eger, G., *Mushroom Science III* (1972). Such biological agents may be encapsulated in the gel capsule substrate of the present invention.

In use, the external surface of the synthetic substrate capsule of the present invention is inoculated with mycelium or spores of fungus. Of course, in a commercial setting a substantial quantity of such capsules are inoculated. Such inoculation may be performed directly by introducing the fungus to the external capsule surface. Alternatively, where fungus is encapsulated in the gel capsule, inoculation of the external capsule surface takes a more indirect route. In such cases, the fungus may experience some growth within the confines of the capsule, but will eventually evade the interior portion of the capsule (perhaps by direct growth through the capsule gel surface, by enzymatic digestion, or physical entry through a fissure in the gel matrix) to inoculate the external capsule surface. In either case, the fungus is grown under particular and controlled temperature, humidity and light conditions that are well known and used in the prior known methods. Under these conditions, mycelium on the external surface of the capsule will grow and penetrate the gel matrix to invade the capsule on which it resides as well as neighboring capsules.

Hereafter, the procedure for best implementing the invention is determined by the intended application thereof. For filamentous fungi used in fermentation processes (e.g., Aspergillus spp.), the present invention is substituted for other solid support matrices common to the art. The bioreactor can be packed with the colonized substrate, or alternatively, it can be packed with uncolonized substrate and inoculated with the fungus in situ.

For mycorrhizal fungi (e.g., *Suillus luteus*) and biocontrol fungi (e.g., Trichoderma spp.), the colonized substrate will replace existing prior known substrates to deliver the fungus to the soil in the vicinity of the targeted plant species.

Where the inoculated substrate serves as a spawn for mushrooms (e.g., *A. bisporus*), the remaining procedure is the same as the other methods known in the art, namely, dispersing the inoculated capsules in a medium which will permit filamentous fungi to produce mushrooms. The medium chosen will depend upon the particular fungi sought to be cultivated. The various media appropriate for a particular fungus are known in the art including compost, straw and wood or wood products (e.g., wood chips or sawdust). For example, *A. bisporus* spawn is usually disseminated in compost; *Pleurotus ostreatus* is usually disseminated in straw; and *Lentinula edodes* is usually disseminated in sawdust. Where the substrate of the present invention also contains nutrients, growth controlling and/or biological agents for the formation of mushrooms, the medium itself may be supplemented with the dispersion of capsules therein.

For *A. bisporus*, after the medium has become colonized by mycelium, it is cased with a casing layer (e.g., soil or peat) to induce the formation of mushrooms. Where the inoculated capsule is to be used as a CACing agent for the production of *A. bisporus* mushrooms from a previously colonized medium, the colonized substrate is thoroughly mixed with the casing material and the resulting casing mixture is spread over the colonized medium in a thin layer (approximately 1.5 inches) to induce the formation of mushrooms. The previously inoculated medium may have been inoculated with the substrate and method of the present invention or by other means (e.g., conventional grain method).

As can be appreciated, the methods and compositions of the present invention can be adapted for use with many species, varieties and strains of filamentous fungi including, but not limited to those listed in Table B below:

TABLE B

*Agaricus augustus*
*Agaricus bisporus*
*Agaricus bitorguis*
*Agaricus campestris*
*Agaricus edulis*
Amanita spp.
Auricularia spp.
*Armillaria mellea*
*Armillaria ponderosa*
Aspergillis spp.
*Boletus chrysenteron*
*Boletus edulis*
*Boletus luteus*
*Boletus mirabilis*
*Boletus zelleri*
Botrytis spp.
*Calvatia gigantea*
*Cantharellus cibarius*
*Cantharellus clavatus*
Cephalosporium spp.
*Ceratocystis ulmi*
*Cercospora apii*
Chaetomium spp.
*Claviceps purpea*
Cochliobolus spp.
Colletotrichium spp.
Coprinus spp.
*Flammulina velutipes*
Fusarium spp.
Laccaria spp.
*Lentinula edodes*
*Morchella angusticeps*
*Morchella conica*
*Morchella crassipes*
*Morchella esculenta*
Mycosoharella spp.
Nectria spp.
Neurospora spp.
*Panaeolus venenosus*
Penicillium spp.
*Pholiota nameko*
Phyllosticta spp.
Phytophthoro spp.
*Pilobolus crystallinus*
*Pilobolus longipes*
Pisolithus spp.
Pleurotus spp.
*Podospora anserina*
*Polyporus sulphureus*
*Psilocybe cubensis*
*Psilocybe mexicana*

TABLE B-continued

Pythium spp.
*Rhizoctonia solani*
Rhizopus spp.
*Schizophyllum commune*
*Sclerotinia sclerotiorum*
Septoria spp.
*Stropharia rugoso-annulata*
*Suillus luteus*
*Trichoderma saturnisporum*
*Trichoderma viride*
*Tremella fuciformis*
Tricholoma spp.
*Verticillium albo-atrum*
*Verticillium fungicola*
*Volvariella volvacea*

It should be recognized that the methods of the present invention may all be carried out under sterile conditions. The gel capsule constituents may all be autoclaved prior to capsule formation and/or the capsules themselves may be autoclaved. Sufficient sterilization is usually achieved by autoclaving for approximately 20 to 60 minutes. Further, the substrate capsules of the present invention may be produced such that their size and contents are uniform, thus creating a reproducible procedure for manufacturing a synthetic substrate for filamentous fungi.

The substrate capsule of the present invention may thus be regarded as a synthetic analog of the prior known grain substrate for spawn or compost substrate for CACing material. However, unlike the prior known natural substrates, the components of the synthetic substrate of the present invention may be manipulated with ease to better promote growth, development and fruiting of fungi. Further, uniformity in size and composition of such capsules may be insured.

These and other aspects of the composition and methods of the present invention may be better appreciated with reference to the following examples:

EXPERIMENTAL

In the following examples, various formulations of the substrate of the present invention were tested to determine their relative abilities to support growth and development of filamentous fungi. Although most of the examples utilize white hybrid types of the common mushroom (*A. bisporus*) as the fungus, the substrates and methods of the invention can be used to cultivate a variety of filamentous fungi. The following examples also explore the relative usefulness of various gel agents, nutrient compositions and texturizing agents.

The various texturizing agents used in the following examples have been heretofore described and are listed in Table C below:

TABLE C

| TEXTURIZING AGENT | DIMENSION |
|---|---|
| fine grade hygramer | 699–1,003 ± 50–100 microns |
| coarse grade hygramer | 1,650–2,150 ± 50–100 microns |
| fine grade vermiculite | 500–800 microns |
| TerraSorb ® | 2,000–3,000 microns |
| ground perlite | 100–6,000 microns |
| cellulose fiber | 100–6,000 microns |
| silica gel | molecular sieve 20–40 |
| sand | 20 grade |
| ground rice hulls | 500–6,000 microns |
| ground rice | 1,000–4,000 microns |
| soy grits | 20–40 mesh |
| fine ground walnut shells | 20 U.S. Standard mesh |
| coarse ground | 10 U.S. Standard mesh |

TABLE C-continued

| TEXTURIZING AGENT | DIMENSION |
| --- | --- |
| walnut shells | |
| saw dust | 600–850 microns |
| ground egg shells | 500–6,000 microns |

In all of the following examples, unless othewise indicated, concentrations of capsule constituents are expressed as percentages of the weight of the constituent (gel agent, nutrient media, additive, texturizing agent or other constituent) in grams/milliliters of water present in the gel mixture prior to complexing.

All sodium alginate used in the following examples was LF60 sodium alginate obtained from Protan, Inc., Drammen, Norway, unless otherwise indicated.

EXAMPLE 1

*A. bisporus* requires good moisture for optimum growth and therefore it is important that the synthetic substrate of the present invention not be unduly prone to desiccation. In this example, the rate of water loss of the capsules of the present invention was compared to that of the conventional organic substrate, pre-cooked rye grain. Smooth surfaced sodium alginate capsules containing only water ("blank capsules"), smooth surfaced sodium alginate capsules containing an aqueous mixture of potato dextrose broth ("PDB capsules") and pre-cooked rye grain were maintained at approximately 23°±2° C. for a period of 21 days. Water loss was determined by reduction in capsule weight and measured at three to five day intervals. Each of the various substrates was tested four times. The results of this experiment are listed in Table I below which indicate that the rate of water loss for blank capsules, PDB capsules and pre-cooked rye grain are not statistically different. The mean value for each treatment is shown as $\bar{x}$.

TABLE I

| Treatment | Replicate | Water Loss (grams)[1] | | | | | |
| --- | --- | --- | --- | --- | --- | --- | --- |
| | | Day 3 | Day 8 | Day 13 | Day 17 | Day 21 | Total |
| blank capsules | 1 | 0.53 | 0.81 | 0.79 | 0.61 | 0.77 | 3.51 |
| | 2 | 0.42 | 0.73 | 0.74 | 0.54 | 0.76 | 3.19 |
| | 3 | 0.06 | 0.85 | 0.59 | 0.42 | 0.61 | 2.53 |
| | 4 | 0.48 | 0.77 | 0.74 | 0.59 | 0.72 | 3.30 |
| | $\bar{x} =$ | 0.37 | 0.79 | 0.72 | 0.54 | 0.72 | 3.14a |
| PDB | 1 | 0.32 | 0.56 | 0.62 | 0.43 | 0.63 | 2.56 |
| | 2 | 0.33 | 0.54 | 0.60 | 0.44 | 0.63 | 2.54 |
| | 3 | 0.34 | 0.55 | 0.61 | 0.44 | 0.63 | 2.57 |
| | 4 | 0.32 | 0.55 | 0.60 | 0.43 | 0.64 | 2.54 |
| | $\bar{x} =$ | 0.32 | 0.55 | 0.61 | 0.44 | 0.63 | 2.55a |
| rye grain | 1 | 0.37 | 0.58 | 0.59 | 0.34 | 0.59 | 2.47 |
| | 2 | 0.42 | 0.63 | 0.63 | 0.48 | 0.62 | 2.78 |
| | 3 | 0.32 | 0.51 | 0.57 | 0.39 | 0.56 | 2.35 |
| | 4 | 0.46 | 0.72 | 0.78 | 0.55 | 0.78 | 3.29 |
| | $\bar{x} =$ | 0.39 | 0.61 | 0.64 | 0.44 | 0.64 | 2.72a |

[1]Means with the same letter are not significantly different at k = 100 (Waller-Duncan Test)

EXAMPLE 2

In this example, the abilities of various synthetic nutrient media to support growth of *A. bisporus* (PSU strain 358) were determined. The compositions of the media tested and the results of this experiment appear in Table II below, which lists the various synthetic media in order of their relative effectiveness. The media tested were all aqueous mixtures of nutrients and additives, the concentrations of which are expressed in terms of percentages (grams nutrient or additive/milliliter water). The media were prepared by mixing nutrient or additive in water and with agar added to a 2% final concentration. For each medium, four 100×15 mm petri plates containing 25 ml of medium were inoculated with a 4 mm mycelial agar plug of the fungus and incubated at 23°±2° C. The effectiveness of each medium was determined by planimetry and expressed in terms of areas of growth which was measured at three to four day intervals.

All media tested, with the exception of the medium composed of 2% brewer's grain+2% supplement+1% safflower oil and the medium composed of 2% brewer's grain+1% safflower oil, supported more vigorous mycelial growth of the fungus than the potato dextrose yeast agar medium.

TABLE II

| Medium | Cumulative Area of Growth (cm$^2$)* | | | | | |
| --- | --- | --- | --- | --- | --- | --- |
| | Day 4 | Day 7 | Day 10 | Day 14 | Day 17 | Day 21 |
| 2% Brewer's grain[1] + 0.5% Grits[2] (pH 6.01) | 0.78ab | 2.43ab | 6.45b | 16.43a | 28.90a | 46.95a |
| 2% Brewer's grain + 2% Grits (pH 6.36) | 0.85a | 2.63a | 7.45a | 17.68a | 30.18a | 44.08a |
| 2% Brewer's grain + 2% Grits + 1% Safflower oil[3] (pH 6.37) | 0.50de | 2.30abc | 5.55c | 13.15bc | 24.88b | 42.93ab |
| 2% Brewer's grain + 0.5% Alfalfa meal[4] (pH 5.88) | 0.55cd | 2.20bc | 5.08cde | 12.93bc | 23.48bc | 41.35abc |
| 2% Brewer's grain + 2% Supplement[5] (pH 6.16) | 0.58cd | 2.08c | 5.18cd | 13.03bc | 21.63bcd | 37.48bcd |
| 2% Brewer's grain + 0.5% Supplement (pH 5.84) | 0.70abc | 2.20bc | 5.60c | 11.83c | 20.23cd | 36.30cd |
| 2% Brewer's grain (pH 5.52) | 0.68bc | 2.23bc | 5.53c | 13.58b | 23.08bc | 33.45de |
| 2% Brewer's grain + 2% Alfalfa meal (pH 6.06) | 0.60cd | 2.05c | 4.53efg | 10.27d | 18.10de | 30.43e |
| 2% Brewer's grain + 2% Alfalfa meal + 1% Safflower oil (pH 6.05) | 0.48de | 1.65de | 3.93hi | 7.95e | 13.63f | 23.93f |
| 0.5% Brewer's grain (pH 5.65) | 0.80ab | 2.50ab | 4.80def | 9.10de | 14.93ef | 22.85f |
| 1% Pectin[6] + 1% Soybean protein[7] + 1% Safflower oil | 0.45de | 2.20bc | 4.40fgh | 7.90e | 12.03fg | 17.20g |

TABLE II-continued

| Medium | Cumulative Area of Growth (cm²)* | | | | | |
|---|---|---|---|---|---|---|
| | Day 4 | Day 7 | Day 10 | Day 14 | Day 17 | Day 21 |
| 2% Brewer's grain + 2% Supplement + 1% Safflower oil (pH 6.18) | 0.40e | 1.60e | 3.40ij | 6.00f | 9.45gh | 14.03gh |
| 2% Brewer's grain + 1% Safflower oil (pH 5.59) | 0.48de | 1.50e | 3.27j | 5.97f | 9.23gh | 12.63gh |
| Potato dextrose yeast agar | 0.80ab | 1.98cd | 3.98ghi | 5.75f | 7.78h | 9.88h |

*Means with the same letter are not significantly different at k = 100 (Waller-Duncan Test).
[1] Dried brewer's grain (Coors, Inc. Golden, CO 80402)
[2] Medium F soy grits (A. E. Stanley Mfg., Co., Decatur, IL 62525)
[3] 100% pure safflower oil (Hollywood Health Foods, Los Angeles, CA 90061)
[4] Alfalfa meal (O. H. Kruze Grain & Milling Co., El Monte, CA 91733)
[5] Nutrisoy defatted soy grits 20-40 (Archer Daniels Midland Co., Decatur, IL 62528)
[6] Citrus pectin, #P-9135 (Sigma Chemical Co., St. Louis, MO 63178)
[7] Soybean protein, #902940 (ICN Nutritional Biochemicals, Cleveland, OH 44128)

In Examples 3-6 which follow, synthetic nutrient media used were prepared by mixing nutrient (and, in some cases, additives) with water forming an aqueous mixture and then adding the gel agent to the aqueous mixture. Sodium alginate was the gel agent used in these examples. The resulting capsules containing the media were made and autoclaved for 20 minutes. The concentrations of the media are expressed as percentages in grams component/milliliter water in the gel mixture. The media are designated as various concentrations of components A, B and C. The medium designated "A" contained ground brewer's grain (dried brewer's grain, Coors, Inc. Golden, Colo. 80402). The medium designated "B" contained equal parts ground brewer's grain and grits (Medium F Soy grits, A. E. Stanley Mfg., Co., Decatur, Ill., 62525). The medium designated "C" contained equal parts ground brewer's grain and supplements (Nutrisoy soy grits, 20-40 mesh, Archer Daniels Midland Co., Decatur, Ill., 62525).

EXAMPLE 3

This example describes further studies of the ability of the synthetic substrate of the present invention to support growth of *A. bisporus* (PSU strain 358) and to serve as spawn to plant compost with the fungus for the production of mushrooms. The gel matrices of all the capsules used in this example were comprised of 1% sodium alginate as the gel agent and 4% fine grade hygramer as the texturizing agent.

Three 250 ml flasks for each of the capsules containing 4% medium B, capsules containing 4% medium C, and pre-cooked rye grain were inoculated with a 4 mm mycelial agar plug of *A. bisporus* and maintained at 23°±2° C. Capsules containing either 4% medium B or 4% medium C were more rapidly colonized with mycelium than conventional rye grain. The capsules showed extensive regrowth of mycelium within 18 hours after shaking. The capsules were fully colonized at 16 days post inoculation. Rye grain, on the other hand, required a full 21 days to achieve the same state of colonization. The growth of *A. bisporus* on synthetic substrates containing medium B or medium C were comparable with perhaps a slightly higher growth rate on the latter formulation.

Samples of each of the inoculated capsules were analyzed by scanning electron microscopy to determine the physical relationship between the mycelium and substrates. It was observed that the fungus grew on the surface as well as within the capsule and rye grain.

Samples of each of the colonized capsules were used to spawn separate 2ft² trays each containing 44 lbs of compost. One tray of compost was through-spawned with 55 grams of medium B capsules and spawned again with 55 grams of medium C capsules 11 days later. One tray of compost was through-spawned with 55 grams of medium C capsules and another tray of compost was through-spawned with 55 grams of conventional rye grain spawn. After a 22 day spawn run at approximately 25° C., the trays were cased with a 1.5 inch thick layer of peat and maintained at 25° C. during case holdings and 18° C. during cropping. The yield of mushrooms was measured over 5 breaks over a total of 35 days.

The results of these croppings are shown in Table III below. All mushrooms produced from the two nutrient capsules tested had apparently normal development and morphology. Trays spawned with the inoculated capsules yielded mushrooms in quantities comparable to or lower than that spawned with rye grain.

It was also observed that rye grain spawn promoted a more rapid colonization of compost than did either the capsule formulations. Because the fungus grew more vigorously on the capsules prior to dissemination in compost than on rye grain, it is reasonable to infer that the relative lower colonization rate with the capsules reflects a depletion of nutrients in the capsule. This hypothesis was supported by the observation that spawning with younger capsules (i.e., those that are not overly colonized) resulted in a more vigorous rate of compost colonization.

TABLE III

| Spawn Substrate | Yield (lbs/ft²) | | | | | |
|---|---|---|---|---|---|---|
| | Break 1 | Break 2 | Break 3 | Break 4 | Break 5 | Total |
| 4% medium B capsules + 4% medium C capsules | 0.83 | 0.22 | 0.63 | 0.28 | 0.02 | 1.98 |
| 4% medium C capsules | 0.46 | 0.40 | 0.33 | 0.19 | 0.22 | 1.60 |
| rye grain | 0.58 | 0.12 | 0.68 | 0.30 | 0.07 | 1.75 |

EXAMPLE 4

In this example, the effectiveness of three texturizing agents on colonization of synthetic substrates by *A. bisporus* was compared to conventional rye grain. All capsules were composed of 1% sodium alginate as gel agent and contained a texturizing agent and a synthetic nutrient medium A, B or C as described above. The three texturizing agents tested were fine grade hygramer, fine ground walnut shells and sawdust. An equal quantity of each substrate was placed into two flasks, inoculated with mycelium of *A. bisporus* (PSU strain 358) and maintained at 23°±2° C. The extent of mycelial colonization of the substrate was rated 15 days after inoculation. The results of this experiment are summarized in Table IV below.

As shown in Table IV below, capsules composed of 4% hygramer and either 4% medium C, 4% medium B or 8% medium B supported a mycelial colonization rate comparable to that of rye grain. Capsules composed of 4% medium C and of either 4% hygramer or 3% sawdust supported a higher rate of growth than the same capsules composed of 8% fine ground walnut shells. Further, the results indicate that increasing the concentration of a nutrient medium (e.g., Medium B) from 2% to 4% or 8% increased the rate of mycelial growth.

Samples of the inoculated substrate were subjected to scanning electron microscopy which revealed that the mycelium grew on the surface of and penetrated fissures on the surface of the capsules.

TABLE IV

| Substrate | Replicate | Colonization of Substrate Score[1] | Mean Score |
|---|---|---|---|
| 4% medium C + | a | 8 | 8 |
| 4% fine grade hygramer | b | 8 | |
| 4% medium C + | a | 4 | 3.5 |
| 8% fine ground walnut shells | b | 3 | |
| 4% medium C + | a | 7 | 6.5 |
| 3% sawdust | b | 6 | |
| 2% medium B + | a | 4 | 5.5 |
| 4% fine grade hygramer | b | 7 | |
| 4% medium B + | a | 8 | 8 |
| 4% fine grade hygramer | b | 8 | |
| 8% medium B + | a | 8 | 8 |
| 4% fine grade hygramer | b | 8 | |
| Rye grain | a | 8 | 8 |
| | b | (C) | |

Rating scale (% colonization): 1 = 0%; 2 = 1–10%; 3 = 11–25%; 4 = 26–50%; 5 = 51–75%; 6 = 76–90%; 7 = 91–99%; 8 = 100%; (C) = contaminated.

EXAMPLE 5

In this example, the colonized capsules and rye grain of Example 4 were evaluated for their ability to support mycelial growth from capsules and into compost. For each treatment, four 50 milliliter graduated cylinders, containing 30 grams of compost, were seeded at the surface with a 0.5 g sample of the colonized substrates and maintained at 25° C. Rates of compost colonization were measured and expressed as linear growth down the cylinders over a period of 15 days at three day intervals. The results of this experiment are summarized in Table V below which demonstrate that the rate of compost colonization of all capsule formulations tested were statistically equivalent to that of rye grain.

TABLE V

| | | Linear Growth of Mycelium in Compost (cm)* | | | | |
|---|---|---|---|---|---|---|
| Substrate | Replicate | Day 3 | Day 6 | Day 9 | Day 12 | Day 15 |
| 4% medium C + | a | 0.3 | 2.3 | 4.6 | 6.9 | 9.7 |
| 4% fine grade | b | 0.6 | 2.3 | 4.9 | 7.1 | 10.0 |
| hygramer | c | 0.5 | 2.5 | 5.2 | 7.5 | 10.1 |
| | d | 0.3 | 3.5 | 3.9 | 6.3 | 8.8 |
| | x = | 0.4ab | 2.7a | 4.7a | 7.0a | 9.7a |
| 4% medium C + | a | 0.5 | 2.3 | 4.9 | 7.2 | 9.5 |
| 8% fine grade | b | 0.8 | 2.3 | 4.6 | 7.0 | 9.7 |
| walnut shells | c | 0.7 | 2.6 | 5.4 | 7.8 | 10.7 |
| | d | 0.8 | 3.2 | 5.3 | 7.9 | 10.3 |
| | x = | 0.7a | 2.6a | 5.1a | 7.5a | 10.1a |
| 4% medium C + | a | 0.4 | 2.0 | 4.2 | 6.6 | 9.3 |
| 3% saw dust | b | 0 | 2.0 | 3.8 | 6.2 | 8.8 |
| | c | 0 | 2.3 | 4.0 | 6.7 | 8.8 |
| | d | 0.5 | 2.5 | 4.8 | 7.2 | 9.6 |
| | x = | 0.2b | 2.2a | 4.2 | 6.7a | 9.1a |
| 2% medium B + | a | 0.2 | 2.2 | 4.3 | 6.5 | 9.2 |
| 4% fine grade | b | 0.2 | 1.8 | 4.4 | 6.8 | 9.5 |
| hygramer | c | 0 | 1.0 | 2.4 | 3.8 | 6.2 |
| | d | 0.8 | 3.1 | 5.5 | 8.0 | 10.9 |
| | x = | 0.3b | 2.0a | 4.2a | 6.3a | 9.0a |
| 4% medium B + | a | 0.7 | 3.7 | 6.1 | 8.3 | 11.0 |
| 4% fine grade | b | 0.4 | 2.3 | 5.2 | 7.7 | 10.2 |
| hygramer | c | 0.4 | 2.4 | 4.5 | 6.4 | 8.9 |
| | d | 0.3 | 1.9 | 3.7 | 6.2 | 8.5 |
| | x = | 0.5a | 2.6a | 4.9a | 7.2a | 9.7a |
| 8% medium B + | a | 0 | 1.7 | 3.8 | 6.1 | 8.2 |
| 4% fine grade | b | 0 | 1.7 | 3.8 | 6.4 | 7.8 |
| hygramer | c | 0.8 | 3.3 | 5.6 | 7.8 | 10.0 |
| | d | 0.7 | 2.2 | 4.5 | 6.8 | 9.6 |
| | x = | 0.4b | 2.2a | 4.4a | 6.8a | 8.9a |
| rye grain | a | 0.4 | 2.3 | 4.7 | 7.3 | 9.9 |
| | b | 0.4 | 2.5 | 4.7 | 7.4 | 10.2 |
| | c | 0.6 | 2.6 | 4.4 | 6.7 | 9.3 |
| | d | 0.3 | 2.1 | 4.0 | 6.0 | 8.3 |
| | x = | 0.4b | 2.2 | 4.5a | 6.9a | 9.4a |

*Means with the same letter are not significantly different at P = 0.05 (Fisher's LSD test).

EXAMPLE 6

In this example, the effects of concentration and composition of the texturizing agent, gel agent, nutrient medium and other capsule inclusions or treatments on the formation of capsules and colonization of capsules after inoculation with *A. bisporus* (PSU strain 358) were studied. In all of the trials, the gel agent was sodium alginate. All capsules were made with a gravity flow system in which the flow rate of the solution and shape of the capsule are dependent upon the viscosity of the solution. The more viscous the solution, the slower the flow rates and the more elongated the capsule. The results of this experiment are shown in Table VI below.

TABLE VI

| Texturizing Agent Conc. | Medium Conc. | Sodium Alginate Conc. | Other Inclusions | Capsule Formation Observations | Post Inoculation Observations |
|---|---|---|---|---|---|
| 4.0% fine grade hygramer | 4.0% Medium C | 1.0% | | Solution flowed smoothly; capsules well formed; slightly elongated, rough surface. | Mycelium colonized capsules well; adhered when shaken; grew well when spawned into compost. Second attempt: growth into compost was slow when compared to rye |

TABLE VI-continued

| Texturizing Agent Conc. | Medium Conc. | Sodium Alginate Conc. | Other Inclusions | Capsule Formation Observations | Post Inoculation Observations |
|---|---|---|---|---|---|
| | | | | | grain spawn; the mycelium preferred to grow in the capsule than into the compost. |
| 4.0% fine grade hygramer | 4.0% Medium C | 1.5% | | Solution flowed moderately slow; capsules firmer than 1.0% alginate. | |
| 4.0% fine grade hygramer | 4.0% Medium C | 2.0% | | Solution flowed slowly; capsules were very firm. | |
| 4.0% fine grade hygramer | 4.0% Medium C | 1.0% | coated with CaCO$_3$ | Solution flowed smoothly, slightly slow; capsules well formed; slightly elongated, rough surface. Capsules became contaminated | |
| 4.0% fine grade vermiculate | 4.0% Medium C | 1.0% | | Solution tended to clog tube; firm & reabsorbent capsules. | |
| 4.0% fine grade hygramer | 6.0% Medium C | 1.0% | | Solution flowed slowly; capsules firm; slightly elongated | |
| 4.0% fine grade hygramer | 2.0% Medium B | 1.0% | | Solution flowed quickly; capsules crumbly, soft. | |
| 4.0% fine grade hygramer | 4.0% Medium B | 1.0% | | Solution flowed smoothly, slightly slow, capsules well formed; slightly elongated, rough surface. | Mycelium colonized capsules well; adhered when shaken; grew well when spawned into compost. |
| 8.0% fine ground walnut shells | 4.0% Medium B | 1.0% | | Formed capsules well; solution flowed slowly; capsules rough, did not hold water well. | Lower rate of mycelial growth when compared to rye grain; also supported a reduced rate of mycelial growth in compost after spawning. |
| 4.0% coarse ground walnut shells | 4.0% Medium B | 1.0% | | Solution flowed slowly; capsules extremely lumpy. | |
| 8.0% coarse ground walnut shells | 4.0% Medium B | 1.0% | | Solution flowed slowly; capsules extremely lumpy. | |
| 2.0% sawdust | 4.0% Medium B | 1.0% | | Solution flowed well; capsules slightly lumpy. | |
| 3.0% sawdust | 4.0% Medium B | 1.0% | | Solution flowed slowly; capsules lumpy and held water well. | Mycelial growth comparable to rye grain; supported a reduced growth rate in compost after spawning. |
| 4.0% rice hulls | 4.0% Medium B | 1.0% | | Solution flowed slowly; rice hull dispersion not uniform. | |
| 4.0% fine ground walnut shells | 4.0% Medium B | 1.0% | coated with CaCO$_3$ | Solution flowed smoothly, slightly slow; capsules well formed; slightly elongated, rough surface. | Capsules became contaminated. |
| 4.0% fine grade hygramer | 2.0% Medium B | 1.0% | | Solution flowed smoothly, slightly slow; capsules well formed; slightly elongated, rough surface. | Mycelium grew slowly on capsules. |
| 4.0% fine grade hygramer | 2.0% Medium B | 1.0% | Coated with CaCO$_3$ | Solution flowed smoothly, slightly slow; capsules well formed; slightly | Capsules became contaminated. |

TABLE VI-continued

| Texturizing Agent Conc. | Medium Conc. | Sodium Alginate Conc. | Other Inclusions | Capsule Formation Observations | Post Inoculation Observations |
|---|---|---|---|---|---|
| | | | | elongated, rough surface. | |
| none | PDB | 0.8% | | Solution flowed smoothly; capsules well formed. | Mycelium grew on capsules but did not adhere when shaken. |
| none | PDB | 1.0% | | Solution flowed smoothly; capsules well formed. | Mycelium grew on capsules but did not adhere when shaken. |
| none | PDB | 1.0% (made aseptically) | | Solution flowed smoothly; capsules well formed. | Mycelium grew on capsules but did not adhere when shaken. |
| none | PDB | 1.5% | | Solution flowed smoothly; capsules well formed. | Mycelium grew on capsules but did not adhere when shaken. |
| none | PDB | 2.0% | | Solution flowed smoothly; capsules well formed. | Mycelium grew on capsules but did not adhere when shaken. |
| none | PDB | 2.0% | 2% glycerol | Solution flowed smoothly; capsules well formed. | Mycelium grew on capsules but did not adhere when shaken. |
| none | PDB | 2.0% | 10% A. bisporus | Solution flowed smoothly; capsules well formed. | Mycelium grew on capsules but did not adhere when shaken. |
| none | PDB | 1.0% | 10% A. bisporus + 1.0% safflower oil | Solution flowed smoothly; capsules well formed. | Mycelium grew on capsules but did not adhere when shaken. |
| 3.0% coarse grade hygramer | PDB | 1.0% | 1.0% safflower oil | Solution viscous; difficult to make capsules; capsules misshapen. | Mycelium colonized quickly; did not ramify compost when spawned. (May have utilized available nutrients.) |
| 3.0% coarse grade hygramer | PDB | 1.0% | | Solution flowed slowly; capsules soft but still firm. | Mycelium colonized and adhered to capsules when shaken. |

EXAMPLE 7

This experiment describes the effects of concentration and composition of gel agent, complexing agent, nutrient medium and other capsule inclusions in the formation of capsules. The texturizing agent in all cases was 4.0% fine grade hygramer. After formation, all capsules were autoclaved for 20 minutes. The results of this experiment are shown in Table VII below.

TABLE VII

| Gel Agent | Nutrient | Complexer | Capsule Formed | Results of Autoclaving |
|---|---|---|---|---|
| 1.0% sodium alginate | 4.0% Medium C | 10 mM CuSO$_4$ | extremely soft | remained intact |
| 1.0% sodium alginate | 4.0% Medium C | 1.0 mM CuSO$_4$ 10 mM CaCl$_2$ | soft | remained intact |
| 1.0% sodium alginate | 4.0% Medium C | 100 mM Ca(NO$_3$)$_2$ | firm | remained intact |
| 1.0% BDH sodium alginate* + 5.0% gelatin | 4.0% Medium C | 100 mM CaCl$_2$ and heat | soft and sticky | remained intact; softened |
| 1.0% potassium alginate | 4.0% Medium C | 100 mM CaCl$_2$ | firm | remained intact |
| 5.0% polygalacturonic acid | 4.0% Medium C | 100 mM CaCl$_2$ | extremely firm-waxy | remained intact; softened |
| 3.0% carageenan | 4.0% QRN** | 100 mM CaCl$_2$ and heat | soft | dissolved |
| 3.0% carageenan | 4.0% QRN** | 500 mM KCl and heat | moderately firm | dissolved |
| 3.0% carageenan | 4.0% QRN** | 500 mM NH$_4$Cl | very firm | dissolved |
| 0.75% carboxymethyl cellulose | 4.0% QRN** | 100 mM CuSO$_4$ | very soft | remained intact |
| 1.0% pectin + 1.0% sodium alginate | 4.0% QRN** | 100 mM CaCl$_2$ | soft | remained intact |
| 1.0% pectin + 1.0% sodium alginate | 4.0% QRN** | 100 mM CuSO$_4$ | soft | remained intact |
| 0.4% carrageenan + 0.5% locust | 4.0% QRN** | 500 mM KCl | very soft | dissolved |

TABLE VII-continued

| Gel Agent | Nutrient | Complexer | Capsule Formed | Results of Autoclaving |
|---|---|---|---|---|
| bean gum 0.4% carrageenan + 0.5% locust bean gum | 4.0% QRN** | 500 mM NH₄Cl | very soft | dissolved |

*BDH sodium alginate obtained from BDH Chemicals, Ltd., Poole, England.
**QRN = "Quick Release Nutrient" (a commercially available fungal nutrient obtained from Fungi Perfecti of Olympia, Washington)

EXAMPLE 8

This example explored the effects of various texturizing agents on capsule formation and growth of *A. bisporus* (PSU strain 358). All capsules were made with 1.0% sodium alginate as the gel agent and complexed with 100 mM $CaCl_2$. The results of this experiment are shown in Table VIII below.

effect on capsule formation and rate of mycelial colonization by *A. bisporus* (PSU strain 358). In all trials, except the blank, the capsules were formed with 1% sodium alginate as the gel agent and 4% fine grade hygramer as the texturizing agent. For each treatment, two 250 ml flasks of substrate were each inoculated with a 6 mm diameter mycelial agar plug of the fungus and maintained at 23°±2° C. Mycelial growth was assessed at 21 days after inoculation. The results of this experiment are summarized in Table IX below.

TABLE VIII

| Texturizing Agents | Nutrient | Capsules Formed | Post Inoculation Mycelial Growth |
|---|---|---|---|
| 4.0% fine grade hygramer | 4.0% Medium C | Firm w/rough surface | Good |
| 8.0% fine ground walnut shells | 4.0% Medium C | Firm w/rough surface | Moderate to poor |
| 4.0% ground rice hulls | 4.0% Medium C | Firm w/slightly rough surface | Moderate |
| 3.0% sawdust | 4.0% Medium C | Firm and spongy w/slightly rough surface | Moderate |
| 4.0% fine grade vermiculite | 4.0% Medium C | Firm, spongy w/rough surface | Moderate to good |
| 1.5% Terrasorb | 4.0% Medium C | Firm w/smooth surface | Good |
| 8.0% sand | 4.0% QRN* | Firm w/slightly rough surface (excessive water loss) | Good on capsules not submerged in unbound water.** |
| 8.0% ground egg shells | 4.0% QRN* | Firm w/slightly rough surface (excessive water loss) | Good on capsules not submerged in unbound water.** |
| 8.0% ground rice | 4.0% QRN* | Firm and sticky with moderately rough surface | Good (profuse) |

*QRN = "Quick Release Nutrient" (a commercially available fungal nutrient obtained from Fungi Perfecti of Olympia, Washington).
**Unbound water refers to free water not bound within the confines of the gel matrix.

EXAMPLE 9

In this example, various amendments as the nutrient source at various concentrations were tested for their

TABLE IX

| Amendment* | | | | | | | Capsule Formation Results | Post Inoculation Evaluations |
|---|---|---|---|---|---|---|---|---|
| 0 | 1 | 2 | 3 | 4 | 5 | 6 | | |
| X** | | | | | | | Solution flowed smoothly; capsule well formed. | Mycelium did not colonize capsules. |
| | 8.0% | | | | | | Solution flowed well; moderately firm capsules. | Growth of mycelium approximately 2 days ahead of rye grain. |
| | | 8.0% | | | | | Solution flowed well; nutrient was absorbant; capsules firm. | Growth of mycelium approximately 2 days ahead of rye grain. |
| | | | 4.0% | | | | Solution flowed well; Higher concentration of solution would not flow. | Growth of mycelium approximately 2 days ahead of rye grain. |
| | | | | 8.0% | | | Solution flowed moderately slow; after autoclaving some nutrient came out of solution. | Growth of mycelium approximately 2 days ahead of rye grain. |
| | | | | | | 12.0% | Solution flowed moderately slow; after autoclaving some nutrient came | Growth of mycelium approximately 2 days ahead of rye grain. |

TABLE IX-continued

| | | Amendment* | | | | | Capsule Formation Results | Post Inoculation Evaluations |
|---|---|---|---|---|---|---|---|---|
| 0 | 1 | 2 | 3 | 4 | 5 | 6 | | |
| | | | | | | 4.0% | out of solution. Solution flowed slowly; would not flow at 6 and 8%. | Growing rapidly when compared to other amendments and rye grain. |
| | 4.0% | 4.0% | | | | | Solution flowed slowly; capsules were firm. | |
| | 4.0% | | | 2.0% | | | Solution flowed well; capsules were firm. | |
| | 4.0% | | | | | 6.0% | Solution flowed well; capsules moderately firm. | |
| | 4.0% | | | | | 6.0% | Solution flowed well; capsules moderately firm (equal to medium C) | |

*Composition of amendments:
1. Nutrisoy defatted soy grits 20–40 (Archer Daniels Midland Co., Decatur, IL 62528)
2. Texturized vegetable protein 118 (Archer Daniels Midland Co., Decatur, IL 62528)
3. StaPro 3000 soybean concentrate (A. E. Stanley Mfg. Co. Decatur, IL 62525)
4. Rocky Mountain Whole Wheat flour. (Honeyville Grain, Inc., Los Angeles, CA 90040)
5. Yellow corn flour (Honeyville Grain, Inc., Los Angelos, CA 90040)
6. Dried brewer's grain (Coors, Inc., Golden, CO 80402)
**Blank - (does not contain any texturizing agent or amendment; sodium alginate concentration at 2%)

EXAMPLE 10

In this example, the effectiveness of the synthetic substrate of the present invention as a CACing agent was studied. For each treatment, a two $ft^2$ tray containing 50 pounds of compost (supplemented at spawning with 2 pounds of Spawn Mate II, a commercially available delayed release nutrient obtained from Spawn Mate, Inc., San Jose, Calif.) was spawned with 110 grams of rye grain colonized with A. bisporus (Swayne's Generation II strain). The results of this experiment are shown in Table X below.

After a 13 day spawn run at 25° C., one tray was cased with 12 pounds of peat (designated as "None" on Table X below); one tray was cased with a mixture of 12 pounds peat and 114 grams of shredded A. bisporus-colonized compost (designated as "Compost" on Table X below); one tray was cased with a mixture of 12 pounds peat and 124 grams of A. bisporus-colonized capsules composed of 1% alginate, 1% cellulose and 4% nutrisoy defatted soy grits 20–40 (designated as "Synthetic, Low Rate" on Table X below); one tray was cased with a mixture of 12 pounds peat and 190 grams of the same colonized capsules (designated as "Synthetic, High Rate" on Table X below); and one tray was cased with a mixture of 12 pounds peat and 127 grams of A. bisporus-colonized millet grain (designated as "Millet" on Table X below). The trays were maintained at 25° C. during case holding and then at 18° C. for cropping. The yield of mushrooms as measured for three breaks over a total of 21 days.

TABLE X

| | Yield ($ft^2$) | | | | |
|---|---|---|---|---|---|
| CACing Agent | Break 1 | Break 2 | Break 3 | Total | Observations |
| None | 1.41 | 1.04 | 0.58 | 3.03 | Mushrooms were dirty, pinned deep; border break; full 6–7 days to harvest each break. |
| Compost | 1.71 | 0.89 | 0.38 | 2.98 | Good even production of mushrooms; clean mushrooms; harvest over 2–3 days per break. |
| Synthetic, Low Rate | 1.59 | 1.02 | 0.31 | 2.92 | Good even production of mushroom; clean mushrooms; harvest about 1.5 to 2 days behind compost; harvest over 3–4 days per break. |
| Synthetic, High Rate | 1.69 | 0.84 | 0.47 | 3.00 | Good even production of mushrooms; clean mushrooms; about 1.5 to 2 days behind compost; harvest over 3—4 days per break. |
| Millet | 1.41 | 0.92 | 0.33 | 2.65 | Good even production of mushrooms; clean mushrooms; harvest over 2–3 days per break. |

EXAMPLE 11

In this example the effect of texturizing agents on colonization of alginate capsules by A. bisporus (PSU strain 361) was studied. For each treatment, three 250 milliliter flasks containing substrate were each inoculated with a 6 millimeter diameter mycelial agar plug of A. bisporus. Mycelial growth was assessed 21 days after inoculation. The results of this example are shown in Table XI.

TABLE XI

| Substrate | Replicate | Score[1] | Colonization of the Substrate Mean Score | Density[2] | Mean Score |
|---|---|---|---|---|---|
| 1% sodium alginate[3] | A | 1 | | 0 | |
| | B | 1 | | | |
| | C | 1 | 1 | 0 | 0 |
| 1% sodium alginate[3] + | A | 3 | | 3 | |
| 4% supplements[4] | B | 4 | | 3 | |
| | C | 5 | 4 | 3 | 3 |
| 1% sodium alginate[3] + | A | 5 | | 3 | |
| 4% supplements[4] + | B | 6 | | 3 | |
| 4% cellulose[5] | C | 5 | 5.3 | 3 | 3 |
| 1% sodium alginate + | A | 5 | | 3 | |
| 4% supplements + | B | 6 | | 3 | |
| 4% fine grade vermiculite[6] | C | 6 | 5.7 | 3 | 3 |
| 1% sodium alginate + | A | 3 | | 2 | |
| 4% supplements + | B | 3 | | 2 | |
| 4% silica gel | C | 3 | 3 | 1 | 1.7 |
| 1% sodium alginate + | A | 3 | | 2 | |
| 4% supplements + | B | 3 | | 2 | |
| 4% sand | C | 2 | 2.7 | 2 | 2 |
| 1% sodium alginate + | A | 5 | | 3 | |
| 4% supplements + | B | 4 | | 3 | |
| 4% perlite[8] | C | 6 | 5 | 3 | 3 |
| rye grain control | A | 6 | | | |
| | B | 5 | | | |
| | C | 6 | 5.7 | 3 | 3 |

[1]Rating scale (% colonization): 1 = 0%; 2 = 1-10%; 3 = 11-25%; 4 = 26-50%; 5 = 51-75%; 6 = 76-90%; 7 = 91-99%; 8 = 100%.
[2]Rating scale (relative density of growth) 0 = none; 1 = light; 2 = moderate; 3 = heavy.
[3]Algin, Kelco Gel LV, Kelco, a division of Merck Co., Inc., Clark, New Jersey, 07066.
[4]Nutrisoy defatted soy grits 20-40 (Archer Daniels Midland Co., Decatur, IL 62528)
[5]Alpha Cellulose fiber (C8002) (Sigma Chemical Co., St. Louis, MO 63178)
[6]Terra-lite (W. R. Grace & Co., Cambridge, MA 02140)
[7]Molecular Sieve 8-12 mesh (J. T. Baker Chemical Co., Phillipsburg, N.J. 08865)
[8]PA-lite 20 (Pennsylvania Perlite Corp., York, PA 17402)

EXAMPLE 12

In this example, the ability of sodium alginate capsules to support the growth of several phylogenetically-diverse filamentous fungi representing three taxonomic classes was evaluated. All capsules were composed of 4% medium C, 1% sodium alginate (obtained from Kelco Gel LV, Kelco, a division of Merck Co., Inc., Clark, N.J.) and 4% vermiculite. For each fungus, two 125 milliliter flasks of capsules were inoculated with a 6 millimeter diameter mycelial agar plug. Mycelial growth at 23°±2° C. was assessed at 4 and 21 days after inoculation.

The results of this experiment are shown on Table XII below. At 4 days after inoculation, the capsules were largely colonized by *Aspergillus niger*, Neurospora spp., Penicillium spp., *Trichoderma viride* and *Rhizopus stolonifer*. *A. bisporus* and *Lentinula edodes* grew more slowly but had fully colonized the substrate by day 21. The inability of some of the tested fungi to grow is probably a result of the well known fact that some fungi have strict nutritional requirements which were not fully met by the nutrient reserve contained in the capsules.

TABLE XII

| | | Colonization of Substrate | | | |
|---|---|---|---|---|---|
| | | Day 4 | | Day 21 | |
| Fungus | Replicate | Score[1] | Mean Score | Score | Mean Score |
| I. Class Basidiomycetes | | | | | |
| *Agarocus bisporus* | A | 2 | | 8 | |
| ("common" mushroom) | B | 2 | 2 | 8 | 8 |
| *Lentinula edodes* | A | 1 | | 8 | |
| ("Shiitake" mushroom) | B | 1 | 1 | 8 | 8 |
| *Pleurotus sajor-caju* | A | 2 | | 2 | |
| ("Phoenix" mushroom) | B | 2 | 2 | 1 (C) | 1.5 |
| *Suilllus luteus* | A | 1 | | 1 | |
| (Mycorrhizal fungus) | B | 1 | 1 | 1 | 1 |
| *Volvariella volvacea* | A | 1 | | 1 | |
| ("Straw" mushroom) | B | 1 | 1 | 1 | 1 |
| II. Class Deuteromycetes | | | | | |
| *Aspergillus niger* | A | 7 | | 8 | |
| ("Black mold") | B | 8 | 7.5 | 8 | 8 |
| Neurospora spp. | A | 8 | | 1 (C) | |
| ("Red bread mold") | B | 8 | 8 | 1 (C) | 1 |
| Penicillium spp. | A | 8 | | 8 | |
| ("Green mold") | B | 8 | 8 | 8 | 8 |
| *Trichoderma viride* | A | 8 | | 8 | |
| ("Green mold") | B | 8 | 8 | 8 | 8 |
| III. Class Zygomycetes | | | | | |
| *Rhizopus stolonifer* | A | 8 | | 8 | |
| ("Common bread mold") | B | 8 | 8 | 8 | 8 |

[1]Rating scale (% colonization): 1 = 0%; 2 = 1-10%; 3 = 11-25%; 4 = 26-50%; 5 = 51-75%; 6 = 76-90%; 7 = 91-99%; 8 = 100%.
(C) Contaminated.

Although the foregoing invention has been described in some detail by way of illustration for purposes of clarity of understanding, it will be understood that numerous modifications may be practiced within the spirit and scope of the appended claims.

We claim:

1. A process for cultivating filamentous fungi comprising the steps of:
   (a) providing a synthetic substrate for filamentous fungi, said substrate comprising:
      a nutrient capable of sustaining growth of said filamentous fungi; and
      a hydrated hydrogel matrix forming a capsule which includes said nutrient therein, said capsule being capable of supporting growth of said filamentous fungi on substantially its entire surface; and (b) inoculating the external surface of said capsule with said filamentous fungi.

2. The process according to claim 1 wherein said nutrient is selected from a group consisting of monosaccharides, oligosaccharides, polysaccharides, sugar acids, alcohols, sugar alcohols, sodium acetate, fatty acids, oils, fats, waxes, amino acids, proteins, nucleosides, nucleotides, sterols, vitamins, cofactors, inorganic compounds, brewer's grain, soybean and soybean derivatives, safflower oil, potato dextrose, alfalfa meal, sugar beet pulp, yeast extract, malt extract, starch, cellulose, hemicellulose, lignocellulose, lignin and compost.

3. The process according to claim 1 wherein said nutrient is included in said hydrated hydrogel matrix at a concentration of at least 1% weight/volume.

4. The process according to claim 1 wherein said hydrated hydrogel matrix is comprised of a gel agent selected from a group consisting of sodium alginate, potassium alginate, polygalacturonic acid and gelatin.

5. The process according to claim 1 wherein said capsule further includes a texturized external surface such that filamentous fungi may adhere thereto.

6. The process according to claim 5 wherein the external surface of capsule is texturized by a texturizing agent capable of physically or chemically creating irregularities on the external surface of said capsule.

7. The process according to claim 6 wherein said texturizing agent is said nutrient.

8. The process according to claim 6 wherein said texturizing agent is an organic or inorganic material.

9. The process according to claim 6 wherein said texturizing agent has moisture absorbent properties.

10. The process according to claim 6 wherein said texturizing agent is particulate in nature and is substantially insoluble in said hydrated hydrogel matrix.

11. The process according to claim 10 wherein said texturizing agent has dimensions in the approximate range of 100 to 6,000 microns.

12. The process according to claim 6 wherein said texturizing agent is selected from a group consisting of minerals, puffed minerals, starches and polymers.

13. The process according to claim 6 wherein said texturizing agent is included in said hydrated hydrogel matrix at a concentration of at least 1% weight/volume.

14. The process according to claim 1 wherein said filamentous fungi have the ability to produce mushrooms and wherein said capsule includes a growth controlling agent for filamentous fungi or mushrooms.

15. The process according to claim 14 wherein said growth controlling agent is a hormone.

16. The process according to claim 1 wherein said filamentous fungi have the ability to produce mushrooms and wherein said capsule provides a biological agent to enhance the growth or development of filamentous fungi or mushrooms.

17. The process according to claim 16 wherein said biological agent is a nematode or a bacterium.

18. The process according to claim 17 wherein said nematode is selected from a group consisting of *Heterorhabditis heliothidis, Neoaplectana carpocapsae* and *Neoaplectana bibionis.*

19. The process according to claim 17 wherein said bacterium is selected from the genus Pseudomonas.

20. The process according to claim 1 wherein said inoculating step comprises directly inoculating the external surface of said capsule with filamentous fungi.

21. The process according to claim 1 wherein said capsule contains filamentous fungi capable of evading the gel capsule and contacting the external surface of said capsule.

22. The process according to claim 1 wherein said filamentous fungi is selected from the genus Agaricus.

23. A process for cultivating mushrooms from filamentous fungi comprising the steps of:
(a) providing a synthetic substrate for filamentous fungi, said synthetic substrate comprising:
a nutrient capable of sustaining growth of said filamentous fungi; and
a hydrated hydrogel matrix forming a capsule which includes said nutrient therein, said capsule being capable of supporting growth of said filamentous fungi on substantially its entire surface;
(b) inoculating the external surface of said capsule with said filamentous fungi; and
(c) dispersing said inoculated capsule into a medium which permits said filamentous fungi to produce mushrooms.

24. The process according to claim 23 wherein said nutrient is selected from a group consisting of monosaccharides, oligosaccharides, polysaccharides, sugar acids, alcohols, sugar alcohols, sodium acetate, fatty acids, oils, fats, waxes, amino acids, proteins, nucleosides, nucleotides, sterols, vitamins, cofactors, inorganic compounds, brewer's grain, soybean and soybean derivatives, safflower oil, potato dextrose, alfalfa meal, sugar beet pulp, yeast extract, malt extract, starch, cellulose, hemicellulose, lignocellulose, lignin and compost.

25. The process according to claim 23 wherein said nutrient is included in said hydrated hydrogel matrix at a concentration of at least 1% weight/volume.

26. The process according to claim 23 wherein said hydrated hydrogel matrix is comprised of a gel agent selected from a group consisting of sodium alginate, potassium alginate, polygalacturonic acid and gelatin.

27. The process according to claim 23 wherein said capsule further includes a texturized external surface such that filamentous fungi may adhere thereto.

28. The process according to claim 27 wherein the external surface of said capsule is texturized by a texturizing agent capable of physically or chemically creating irregularities on the external surface of said capsule.

29. The process according to claim 28 wherein said texturizing agent is said nutrient.

30. The process according to claim 28 wherein said texturizing agent is an organic or inorganic material.

31. The process according to claim 28 wherein said texturizing agent has moisture absorbent properties.

32. The process according to claim 28 wherein said texturizing agent is particulate in nature and is substantially insoluble in said hydrated hydrogel matrix.

33. The process according to claim 32 wherein said texturizing agent has dimensions in the approximate range of 100 to 6,000 microns.

34. The process according to claim 28 wherein said texturizing agent is selected from a group consisting of minerals, puffed minerals, starches and polymers.

35. The process according to claim 28 wherein the said texturizing agent is included in said hydrated hydrogel matrix at a concentration of at least 1% weight/volume.

36. The process according to claim 23 wherein said capsule includes a growth controlling agent for filamentous fungi or mushrooms.

37. The process according to claim 36 wherein said growth controlling agent is a hormone.

38. The process according to claim 23 wherein said capsule provides a biological agent to enhance the growth or development of filamentous fungi or mushrooms.

39. The process according to claim 38 wherein said biological agent is a nematode or a bacterium.

40. The process according to claim 39 wherein said nematode is selected from a group consisting of *Heterorhabditis heliothidis, Neoaplectana carpocapsae* and *Neoaplectana bibionis.*

41. The process according to claim 39 wherein said bacterium is selected from the genus Pseudomonas.

42. The process according to claim 23 wherein said inoculating step comprises directly inoculating the external surface of said capsule with filamentous fungi.

43. The process according to claim 23 wherein said capsule contains filamentous fungi capable of evading the gel capsule and contacting the external surface of said capsule.

44. The process according to claim 23 wherein said medium which permits said filamentous fungi to produce mushrooms is selected from a group consisting of compost, straw, wood and wood products.

45. The process according to claim 23 further comprising the step of covering said medium of step (c) having said inoculated capsule dispersed therein with a thin layer of a second medium containing a further quantity of said inoculated capsule.

46. The process according to claim 45 wherein said second medium is selected from a group consisting of peat and soil.

47. The process according to claim 23 further comprising the step of covering a second medium previously inoculated with filamentous fungi with a thin layer of the medium of step (c) having said inoculated capsule dispersed therein.

48. The process according to claim 47 wherein said second medium is selected from a group consisting of compost, straw, wood and wood products.

49. The process according to claim 23 wherein said filamentous fungi is selected from the genus Agaricus.

50. A process for cutivating mushrooms from filamentous fungi comprising the steps of:
providing a nutrient capable of sustaining growth of said filamentous fungi;
including an inoculum of said filamentous fungi in the capsule along with said nutrient; and
providing a hydrated hydrogel matrix forming a capsule which includes said nutrient and said filamentous fungi therein.

51. The process according to claim 50 wherein said nutrient is selected from a group consisting of monosaccharides, oligosaccharides, polysaccharides, sugar acids, alochols, sugar alcohols, sodium acetate, fatty acids, oils, fats, waxes, amino acids, proteins, nuceleosides, nucleotides, sterols, vitamins, cofactors, inorganic compounds, brewer's grain, soybean and soybean derivatives, safflower oil, potato dextrose, alfalfa meal, sugar beet pulp, yeast extract, malt extract, starch, cellulose, hemicellulose, lignocellulose, lignin and compost.

52. The process according to claim 50 wherein said nutrient is included in said hydrated hydrogel matrix at a concentration of at least 1% weight/volume.

53. The process according to claim 50 wherein said hydrated hdyrogel is comprised of a gel agent selected from a group consisting of sodium alginate, potassium alginate, polygalacturonic acid and gelatin.

54. The process according to claim 50 including the step of texturizing the external surface of said capsule such that filamentous fungi may adhere thereto.

55. The process according to claim 54 wherein said step of texturizing comprises contacting the capsule with a texturizing agent or including said texturizing agent in the hydrogel matrix, wherein said texturizing agent is capable of physically or chemically creating irregularities on the external surface of said capsule.

56. The process according to claim 55 wherein said texturizing agent is said nutrient.

57. The process according to claim 55 wherein said texturizing agent is an organic or inorganic material.

58. The process according to claim 55 wherein said texturizing agent has moisture absorbent properties.

59. The process according to claim 55 wherein said texturizing agent is particulate in nature and is substantially insoluble in said hydrated hydrogel matrix.

60. The process according to claim 59 wherein said texturizing agent has dimensions in the approximate range of 100 to 6,000 microns.

61. The process according to claim 55 wherein said texturizing agent is selected from a group consisting of minerals, puffed minerals, starches and polymers.

62. The process according to claim 55 wherein the concentration of said texturizing agent in said hydrated hydrogel is at least 1% weight/volume.

63. The process according to claim 50 wherein said filamentous fungi have the ability to produce mushrooms and wherein said capsule includes a growth controlling agent for filamentous fungi or mushrooms.

64. The process according to claim 63 wherein said growth controlling agent is a hormone.

65. The process according to claim 50 wherein said filamentous fungi have the ability to produce mushrooms and wherein said capsule provides a biological agent to enhance the growth or development of filamentous fungi or mushrooms.

66. The process according to claim 65 wherein said biological agent is a nematode or a bacterium.

67. The process according to claim 66 wherein said nematode is selected from a group consisting of *Heterorhabditis heliothidis, Neoaplectana carpocapsae* and *Neoaplectana bibionis.*

68. The process according to claim 66 wherein said bacterium is selected from the genus Pseudomonas.

69. The process according to claim 50 wherein said filamentous fungi is selected from the genus Agaricus.

70. A synthetic substrate for filamentous fungi comprising:
a nutrient capable of sustaining growth of said filamentous fungi;
an inoculum of said filamentous fungi; and
a hydrated hdrogel matrix forming a capsule which includes at least said nutrient therein, said capsule being capable of supporting growth of said filamentous fungi on substantially its entire surface.

71. The synthetic substrate according to claim 70 wherein said nutrient is selected from a group consisting of monosaccharides, oligosaccharides, polysaccharides, sugar acids, alcohols, sugar alcohols, sodium acetate, fatty acids, oils, fats, waxes, amino acids, proteins, nucleosides, nucleotides, sterols, vitamins, cofactors, inorganic compounds, brewer's grain, soybean and soybean derivatives, safflower oil, potato dextrose, alfalfa meal, sugar beet pulp, yeast extract, malt extract, starch, cellulose, hemicellulose, lignocellulose, lignin and compost.

72. The synthetic substrate according to claim 71 nutrient is included in said hydrated hydrogel matrix at a concentration of at least 1% weight/volume.

73. The synthetic substrate according to claim 70 wherein said hydrated hydrogel is comprised of a gel agent selected from a group consisting of sodium alginate, potassium alginate, polygalacturonic acid and gelatin.

74. The synthetic substrate according to claim 70 further comprising means for texturizing the external surface of said capsule such that filamentous fungi may adhere thereto.

75. The synthetic substrate according to claim 74 wherein said means for texturizing comprises a texturizing agent capable of physically or chemically creating irregularities on the external surface of said capsule.

76. The synthetic substrate according to claim 75 wherein said texturizing agent is said nutrient.

77. The synthetic substrate according to claim 75 wherein said texturizing agent is an organic or inorganic material.

78. The synthetic substrate according to claim 75 wherein said texturizing agent has moisture absorbent properties.

79. The synthetic substrate according to claim 75 wherein said texturizing agent is particulate in nature and is substantially insoluble in said hydrated hydrogel matrix.

80. The synthetic substrate according to claim 79 wherein said texturizing agent has dimensions in the approximate range of 100 to 6,000 microns.

81. The synthetic substrate according to claim 75 wherein said texturizing agent is selected from a group consisting of minerals, puffed minerals, starches and polymers.

82. The synthetic substrate according to claim 70 wherein said texturizing agent is included in said hydrated hydrogel at a concentration of at least 1% weight/volume.

83. The synthetic substrate according to claim 70 wherein said filamentous fungi is capable of producing mushrooms and wherein said capsule includes a growth controlling agent for filamentous fungi or mushrooms.

84. The synthetic substrate according to claim 83 wherein said growth controlling agent is a hormone.

85. The synthetic substrate according to claim 71 wherein said filamentous fungi is capable of producing mushrooms and wherein said capsule provides a biological agent to enhance the growth or development of filamentous fungi or mushrooms.

86. The synthetic substrate according to claim 85 wherein said biological agent is a nematode or a bacterium.

87. The synthetic substrate according to claim 86 wherein said nematode is selected from a group consisting of *Heterorhabditis heliothidis*, *Neoaplectana carpocapsae* and *Neoaplectana bibionis*.

88. The synthetic substrate according to claim 86 wherein said bacterium is selected from the genus Pseudomonas.

89. The synthetic substrate according to claim 70 wherein said capsule contains said filamentous fungi.

90. The synthetic substrate according to claim 70 wherein the external surface of said capsule has been inoculated with said filamentous fungi.

91. The synthetic substrate according to claim 70 wherein said filamentous fungi is selected from the genus Agaricus.

92. A synthetic CACing agent for covering a first medium having filamentous fungi colonized therein to induce said filamentous fungi to produce mushrooms, wherein said first medium permits said filamentous fungi to produce mushrooms, said CACing agent comprising:

a substrate inoculated with filamentous fungi, said substrate comprising a nutrient capable of sustaining growth of filamentous fungi, said nutrient included in a hydrated hydrogel matrix forming a capsule, said capsule being capable of supporting growth of said filamentous fungi on substantially its entire surface; and a second medium having said inoculated substrate dispersed therein.

93. The synthetic CACing agent according to claim 92 wherein said nutrient is selected from a group consisting of monosaccharides, oligosaccharides, polysaccharides, sugar acids, alcohols, sugar alcohols, sodium acetate, fatty acids, oils, fats, waxes, amino acids, proteins, nucleosides, nucleotides, sterols, vitamins, cofactors, inorganic compounds, brewer's grain, soybean and soybean derivatives, safflower oil, potato dextrose, alfalfa meal, sugar beet pulp, yeast extract, malt extract, starch, cellulose, hemicellulose, lignocellulose, lignin and compost.

94. The synthetic CACing agent according to claim 92 wherein said nutrient is included in said hydrated hydrogel matrix at a concentration of at least 1% weight/volume.

95. The synthetic CACing agent according to claim 92 wherein said hydrated hydrogel is comprised of a gel agent selected from a group consisting of sodium alginate, potassium alginate, polygalacturonic acid and gelatin.

96. The synthetic CACing agent according to claim 92 further comprising means for texturizing the external surface of said capsule such that filamentous fungi may adhere thereto.

97. The synthetic CACing agent according to claim 96 wherein said means for texturizing comprises a texturizing agent capable of physically or chemically creating irregularities on the external surface of said capsule.

98. The synthetic CACing agent according to claim 97 wherein said texturizing agent is said nutrient.

99. The synthetic CACing agent according to claim 97 wherein said texturizing agent is particulate in nature and is substantially insoluble in said hydrated hydrogel matrix.

100. The synthetic CACing agent according to claim 97 wherein said texturizing agent is an organic or inorganic material.

101. The synthetic CACing agent according to claim 97 wherein said texturizing agent has moisture absorbent properties.

102. The synthetic CACing agent according to claim 97 wherein said texturizing agent has dimensions in the approximate range of 100 to 6,000 microns.

103. The synthetic CACing agent according to claim 97 wherein said texturizing agent is selected from a group consisting of minerals, puffed minerals, starches and polymers.

104. The synthetic CACing agent according to claim 92 wherein said texturizing agent is included in said hydrated hydrogel at a concentration of at least 1% weight/volume.

105. The synthetic CACing agent according to claim 92 wherein said capsule includes a growth controlling agent for filamentous fungi or mushrooms.

106. The synthetic CACing agent according to claim 105 wherein said growth controlling agent is a hormone.

107. The synthetic CACing agent according to claim 92 wherein said capsule provides a biological agent to enhance the growth or development of filamentous fungi or mushrooms.

108. The synthetic CACing agent according to claim 107 wherein said biological agent is a nematode or a bacterium.

109. The synthetic CACing agent according to claim 108 wherein said nematode is selected from a group consisting of *Heterorhabditis heliothidis, Neoaplectana carpocapsae* and *Neoaplectana bibionis.*

110. The synthetic CACing agent according to claim 108 wherein said bacterium is selected from the genus Pseudomonas.

111. The synthetic CACing agent according to claim 92 wherein said capsule contains filamentous fungi.

112. The synthetic CACing agent according to claim 92 wherein said second medium is selected from a group consisting of peat and soil.

113. The synthetic CACing agent according to claim 92 wherein said filamentous fungi is selected from the genus Agaricus.

* * * * *

UNITED STATES PATENT AND TRADEMARK OFFICE
CERTIFICATE OF CORRECTION

PATENT NO. : 4,803,800
DATED : Feb. 14, 1989
INVENTOR(S) : C. Peter Romaine et al.

It is certified that error appears in the above - identified patent and that said Letters Patent is hereby corrected as shown below:

Title page:

Assignee is incorrect. Add --Research Corporation Technologies, Inc.-- after "Plant Genetics, Inc."

Column 2, line 19, after "in" insert --nutrients for the fruiting stage with mushroom spawn.--.

Column 28, Table XII, "Agarocus" should be --Agaricus--.

Column 32, line 56, "hdrogel" should be --hydrogel--.

Signed and Sealed this

Third Day of October, 1989

Attest:

DONALD J. QUIGG

Attesting Officer

Commissioner of Patents and Trademarks